United States Patent
Xu et al.

(10) Patent No.: US 9,889,173 B2
(45) Date of Patent: Feb. 13, 2018

(54) COMPOSITION FOR IMPROVING MACULAR PIGMENT DENSITY AND PREVENTING OR TREATING AGE-RELATED MACULAR DEGENERATION

(71) Applicant: Zhejiang Medicine Co., Ltd. Xinchang Pharmaceutical Factory, Xinchang County (CN)

(72) Inventors: Xinde Xu, Xinchang County (CN); Lihua Zhang, Xinchang County (CN); Xiaoxia Sun, Xinchang County (CN)

(73) Assignee: Zhejiang Medicine Co., Ltd. Xinchang Pharmaceutical Factory, Zhejiang Province (CN)

( * ) Notice: Subject to any disclaimer, the term of this patent is extended or adjusted under 35 U.S.C. 154(b) by 360 days.

(21) Appl. No.: 14/419,938

(22) PCT Filed: Aug. 8, 2013

(86) PCT No.: PCT/CN2013/000933
§ 371 (c)(1),
(2) Date: Feb. 6, 2015

(87) PCT Pub. No.: WO2014/023082
PCT Pub. Date: Feb. 13, 2014

(65) Prior Publication Data
US 2015/0182577 A1    Jul. 2, 2015

(30) Foreign Application Priority Data

Aug. 8, 2012 (CN) .......................... 2012 1 0279700

(51) Int. Cl.
| | | |
|---|---|---|
| A61K 36/82 | (2006.01) |
| A61K 36/185 | (2006.01) |
| A61K 31/047 | (2006.01) |
| A61K 31/045 | (2006.01) |
| A61K 31/07 | (2006.01) |
| A61K 31/353 | (2006.01) |
| A61K 31/355 | (2006.01) |
| A61K 31/375 | (2006.01) |
| A61K 33/04 | (2006.01) |
| A61K 33/00 | (2006.01) |
| A61K 33/34 | (2006.01) |
| A61K 31/05 | (2006.01) |
| A61K 31/015 | (2006.01) |

(52) U.S. Cl.
CPC ............ *A61K 36/82* (2013.01); *A61K 31/015* (2013.01); *A61K 31/045* (2013.01); *A61K 31/047* (2013.01); *A61K 31/05* (2013.01); *A61K 31/07* (2013.01); *A61K 31/353* (2013.01); *A61K 31/355* (2013.01); *A61K 31/375* (2013.01); *A61K 33/00* (2013.01); *A61K 33/04* (2013.01); *A61K 33/34* (2013.01)

(58) Field of Classification Search
None
See application file for complete search history.

(56) References Cited

U.S. PATENT DOCUMENTS 6,329,432 B2 * 12/2001  Howard ................ A23L 33/155
514/725

FOREIGN PATENT DOCUMENTS

| AU | 2008229662 A1 * | 4/2009 |
| JP | 2001270832 A    * | 10/2001 |

* cited by examiner

*Primary Examiner* — Chris R Tate
*Assistant Examiner* — Randall Winston
(74) *Attorney, Agent, or Firm* — Ash Tankha; Lipton, Weinberger & Husick

(57) ABSTRACT

The present invention provides a composition for improving macular pigment optical density and preventing or treating age-related macular optical degeneration. The composition comprises lutein, zeaxanthin and tea extracts, wherein the weight ratio of zeaxanthin to lutein is more than or equal to 1. The composition may prevent formation of choroidal neovascularization to achieve effects on comprehensively preventing or treating age-related macular optical degeneration (AMD).

8 Claims, 3 Drawing Sheets

COMPOSITION FOR IMPROVING MACULAR PIGMENT DENSITY AND PREVENTING OR TREATING AGE-RELATED MACULAR DEGENERATION

CROSS REFERENCE TO RELATED APPLICATIONS

This application is a national phase application of the PCT international application number PCT/CN2013/000933 titled "Composition Used For Improving Macular Pigment Density In Eyes And Preventing Or Treating Age-related Macular Degeneration", filed in the State Intellectual Property Office of the People's Republic of China on Aug. 8, 2013, which claims priority to and the benefit of Chinese patent application number 201210279700.X filed in the State Intellectual Property Office of the People's Republic of China on Aug. 8, 2012, The specifications of the above referenced patent applications are incorporated herein by reference in their entirety.

FIELD OF THE INVENTION

The present invention relates to a composition for improving macular pigment optical density and preventing or treating age-related macular degeneration, and belongs to fields of pharmaceutical industry.

BACKGROUND OF THE INVENTION

Age-related macular degeneration (AMD) is a major human blindness disease. It often leads to central vision loss during an attack, and even makes blindness seriously. The incidence of age-related macular degeneration associates with ages. The disease easily happens with getting older. The survey shows that 15 million people having more than 50 years old are suffering from this disease in North America, 1.2 million people of which are in serious condition. 30% of population over 75 years in the United States is suffering from macular degeneration in certain degree, and 23% of population over 75 years in the United States will suffer from macular degeneration in next five years. Some surveys show that the incidence of macular degeneration is respectively 16.8%, 25.6% and 42% for the age of 55-64, 65-74 and over the age of 75 of people.

There are two types of un-exudative (dry) and exudative (wet) macular degeneration. The two types of macular degeneration reflect different pathological processes, and usually occur on the two eyes of patients simultaneously, and it will develop deeply if without intervention.

Both of the dry and wet macular degeneration are accompanied with formation of drusen in eyes. Drusen is a kind of small spots from irregular round yellow to white frogspawn, transparent or translucent between retinal pigment epithelium and Bruch's membrane. The drusen always means pathological changes of retinal pigment epithelium function. The drusen has two of hard and soft forms. The hard drusen (tuberculiform) is due to accumulation of retinal epithelial cells metabolism fragment on the Bruch's membrane. The soft drusen is generally larger than the hard drusen and without clear boundary, and is usually formed by shed of retinal epithelial cells. The drusen will light after calcification. Dry macular degeneration often leads to atrophy and degeneration of external retinal, retinal epithelial cells, Bruch's membrane or choriocapillaris, to form drusen, color disorder and other eyes dysfunction. The wet macular degeneration is characterized in that pulpiness or hemorrhagic detachment of retina epithelial cells or sensory nerve layers, will lead to formation of choroidal neovascularization. These could cause visual distortion or blurred central vision in clinic, seriously may result in blindness.

As mentioned above, AMD is eye diseases resulting in blindness. This is because a fluorescent lipofuscin formed by lipid oxidation in eyes, leads to formation of drusen, Bruch's membrane and choroidal neovascularization. It is believed that eyes exposed to high energy blue light for long-term can accelerate lipofuscin formation. At present, the mechanism of AMD formation is unclear, no specific method of treatment or prevention is provided. However many researches show that formation and development of AMD closely relates to amounts of carotenoids in eyes, especially contents of lutein and zeaxanthin. Large amount of lutein and zeaxanthin can delay occurrence and formation of AMD. In addition, antioxidants of the body such as vitamin E, vitamin A, selenium, zinc and glutathione can also play an inhibitory effect on the development of AMD.

Lutein and zeaxanthin are merely two carotenoids in the human retina and are selectively deposited in macular region and the retina, have the highest density around the macular fovea center and a gradually decreased density around the retina. These macular pigments can effectively prevent from occurrence of oxidation reaction in retina. It could be assumed that an effective method of treating or preventing macular degeneration or injury is to supple for lutein and zeaxanthin. The good health effect on AMD made by lutein and zeaxanthin is mainly because lutein and zeaxanthin have the maximum absorption wavelength around 450 nm to be consistent with the blue light wavelength in visible light. Lutein and zeaxanthin in fundus macular can have a good filtering effect to absorb and filter destructive blue lights, in order to protect eyes and reduce lipid oxidation, delay occurrence and development of AMD. Furthermore, lutein and zeaxanthin can be used to improve visual efficacy such as juvenile myopia and senile blindness caused by muscle degeneration and eye damage caused by the ultraviolet radiation from sunlight and computer in the absence of AMD. Lots of clinical tests results show that the intake of lutein and zeaxanthin is 6 mg per dayin human body. It is thought that the carotenoid yellow dermatosis could not bring about if the acceptable daily intake (ADI) of lutein crystal is 25 mg/person/day.

More and more people are interested in special physiological functions of lutein and zeaxanthin. Currently, a large amount of healthy food and fortified food containing two natural pigments of lutein and zeaxanthin are present abroad. The FDA of USA approved uses of lutein and zeaxanthin as food supplement agents to improve nutritive values in 1995.

Lutein and zeaxanthin can't be synthesized in human body and must be ingested from outside. Currently lutein can only be extracted from plants mainly marigold flowers due to its asymmetry structure. Zeaxanthin is mainly derived from three sources such as extracting from matrimony vine plants, chemical synthesizing and obtaining by lutein isomerization transposition reaction. Zeaxanthin extracted from plants and by chemical synthesis is (3R, 3'R) stereoisomeric zeaxanthin. The one obtained from isomerization of lutein is (3R, 3'S) isomer. Both of (3R, 3'R)-zeaxanthin and (3R ,3'S, meso)-zeaxanthin are distributed in human eyes, in particular, the proportion of (3R , 3'S, meso)-zeaxanthin close to the visual center is higher.

More and more people are engaged in researches of lutein and zeaxanthin and many products of treating and preventing fundus macular degeneration (AMD) through lutein and zeaxanthin are present in the market, based on understanding on function and perfection of laws of lutein and zeaxanthin for visual health. These studies or products often focus on functions of lutein and zeaxanthin. However it hasn't reported that the complex use of lutein and zeaxanthin, especially lutein cooperating with large amount of zeaxanthin, and a certain amount of plant polyphenols antioxidants is used to treating or preventing AMD.

U.S. Pat. No. 7,282,225 B1 discloses a dietary supplement comprising various vitamins, minerals, carotenoids, antioxidants and plant extracts. The dietary supplement is beneficial to enhance visual function and acuity, and is helpful to treat or prevent macular degeneration. Wherein it uses a variety of plant extracts to be limited, and complex composition, and but it doesn't notice special efficacy of zeaxanthin.

US 2009/0155381 A1 describes a medication comprising lutein and/or zeaxanthin and many antioxidants for treating or preventing age-related macular degeneration. But this formula does not mention the important role of zeaxanthin in visual health.

US 2009/0181901 A1 introduces a substance containing—SH functional group or the mixer thereof with anthocyanin used for increasing the bioavailability of carotenoid including lutein in body.

US 2010/0330171A1 describes a nutritional supplement contributing to visual health, consisting of an anti-oxidant component, an anti-inflammatory component and an anti-angiogenic component, wherein the supplement comprises tocotrienol and green tea extract.

U.S. Pat. No. 7,887,847 B2 reveals a dietary component comprising vitamin E, minerals, polyunsaturated fatty acids, lutein and zeaxanthin. Wherein the weight ratio of lutein to zeaxanthin is around 20:1 and the amount of zeaxanthin is less.

U.S. Pat. No. 7,267,830 B2 presents a dietary supplement for delaying macular degeneration and improving visual health, comprising vitamin E, lutein and zeaxanthin, copper, zinc, DHA, rosemary extract and other vitamins and minerals, etc., the formula is complicated, and the weight ratio of lutein to zeaxanthin is around 2:1.

U.S. Pat. No. 6,329,432 B2 analyzes distribution of zeaxanthin stereoisomer in human eyes. It is considered that the content of zeaxanthin is higher close to the macular center relative to lutein, especially the content of meso-zeaxanthin in the visual macular reaches the highest concentration at the midpoint of macular center. It implies that they play an important role in visual health especially in delaying processes of AMD diseases. But it only emphasizes effects of meso-zeaxanthin of preventing or treating AMD in the patent, neither reminds synergistic effects of zeaxanthin and lutein, nor reminds synergistic effects of other substances.

All of the above applications or patents are to provide dietary supplements mixing one or several vitamins, antioxidants, plant extracts with lutein and zeaxanthin, to act as effects of delaying or treating macular recession. But it just emphasizes functions of lutein in these formulas, no deeply researches on eyes' function of zeaxanthin is provided. In fact, zeaxanthin has one conjugated double bond more than lutein in molecular structure, it makes zeaxanthin have stronger antioxidant activity than lutein, and plays an important role in human visual health. Some researches in 1980's also proved that substances in the eye macular center is mainly zeaxanthin, the amount of zeaxanthin gradually reduces, the amount of lutein subsequently increases when concentrically away from recess and close to the outer peripheral of the macular, and lutein is the major yellow pigment in the periphery of the macular.

It can also be seen from changes of proportion of lutein to zeaxanthin in nature and different parts of body tissues that the proportion of lutein to zeaxanthin in marigold flowers of lutein raw materials is around 10~12:1, this proportion in human blood is around 3~5:1, the proportion of lutein to zeaxanthin in the macular periphery is 3:1, but, the proportion of lutein to zeaxanthin in the macular center is completely reversed and is 1:3, The change of the proportion of lutein to zeaxanthin in the different parts of the eyes shows that the zeaxanthin especially meso-zeaxanthin plays an important and unique role in human visual health. If the proportion of lutein to zeaxanthin in dietary supplement 我 would be determined by the proportion of lutein to zeaxanthin in macular center, it would strengthen the concentration of zeaxanthin in eyes and would play better effects of delaying AMD.

In addition, it would play unexpected effects when moderately adding some plant extracts in order to prevent or delay formation of choroidal neovascularization caused by pulpiness or hemorrhagic detachment of the retina epithelial cells or sensory nerve layers before and after AMD disease. Green tea extracts among these plant extracts would be worth watching. Green tea polyphenols mainly comprises four components such as GC (gallocatechin), CG (catechin gallate), GCG (gallocatechin gallate). The epigallocatechin gallate (EGCG) has the highest activity in the green tea polyphenols. Epidemiological studies revealed that EGCG has the ability of resisting formation of blood vessels and reduces the incidence of diabetes proliferative vascular hyperplastic lesions. Angiogenesis in ocular neovascularization is of great significance for damage of structure and function of the eyes. It is further found that green tea polyphenols can significantly inhibit proliferation of endothelial cells in a dose-dependent manner, and can lead to cell arrest in G1 phase. So green tea polyphenol is one of effective and prospective drugs of anti-angiogenesis.

SUMMARY OF THE INVENTION

The present invention provides a composition for improving Macular Pigment Optical Density (MPOD) in eyes and preventing or treating the age-related macular optical degeneration. The composition comprises lutein, zeaxanthinand and tea extracts. A weight ratio of zeaxanthin to lutein is more than or equal to 1.

Preferably, the weight ratio of zeaxanthin to lutein is 2:1~3:1.

Preferably, the amount of zeaxanthin or lutein is respectively 2 mg~120 mg, more preferably 6 mg~20 mg.

Wherein zeaxanthin is (3R, 3'R)-zeaxanthin extracted from plants or obtained by chemical synthesis according to conventional methods, or (3R, 3'S)-zeaxanthin obtained by isomerization transposition from lutein as raw materials. Lutein and zeaxanthin is respectively in the form of free crystal or fatty acid ester.

Preferably, the tea extract is a mixture of GC, CG, GCG and EGCG, or EGCG. The amount of the tea extract or EGCG is respectively 10 mg~200 mg, preferably 20 mg~120 mg.

Preferably, the composition further comprises vitamins, antioxidants and/or trace element; wherein the vitamins is selected from the group consisting of vitamin C, vitamin E, natural vitamin E and vitamin A; the antioxidants is beta-carotene, polyunsaturated fatty acids and/or plant extract blueberry polyphenols; the trace element is copper, zinc and/or selenium.

As mentioned above, age-related macular disease (AMD) is a kind of senile disease with higher incidence, and this disease is irreversible. Currently, no effective treatment is provided, an effective way for AMD disease is to prevent or delay treatment. Researches have recently shown that the incidence of AMD disease is negatively correlated with the content of lutein and zeaxanthin in human blood and eyes, lutein and zeaxanthin are merely two pigments in the human eye macular pigment. These indicate that lutein and zeaxanthin play an important role in processes of preventing and treating AMD. The occurrence and development of AMD diseases can get a good hint through monitoring changes of Macular Pigment Optical Density (MPOD) in eyes.

Furthermore, the amount of zeaxanthin in blood is not dominant relative to lutein. But it is closer to the center of visual macula, the amount of zeaxanthin in the human visual macula is higher. Especially in the midpoint of the visual macula, not only the weight ratio of zeaxanthin to lutein is more than 3:1, but also it appears a quantity of meso-zeaxanthin not to exist in the blood. These show that zeaxanthin may plays a very important role in visual health. From the point of molecular structure, zeaxanthin has one conjugated double bond more than lutein, and its antioxidant activity and ability of absorbing high energy blue light of zeaxanthin are better than that of lutein in theory.

Zeaxanthin in eyes mainly has two forms, in particular, (3R, 3'R) isomer and (3R, 3'S) isomer, (3S, 3'S) isomer only exists in macular central with trace amounts. In the two isomers, (3R, 3'R) isomer is transferred to macular after ingesting from outside and absorbing into the blood, (3R, 3'S) isomer is obtained through isomerization transposition of lutein under actions of certain enzyme in the retina. So supplying zeaxanthin alone can ensure the amount of zeaxanthin in blood or macular, but not ensure supplyment of lutein in the body, and the isomer configuration of zeaxanthin in body is the same as that of zeaxanthin intaked, according to current studies. Part of lutein in retina can be converted into meso-zeaxanthin [(3R, 3'S, meso)-zeaxanthin] if supplying lutein alone. But the transformation will be limited by levels of invertase in individual. It may cause quantities of meso-zeaxanthin in the midpoint of the macular not enough and affects functions of visual macular.

In order to achieve the purpose of visual health, it is the best to supply lutein and zeaxanthin for the body simultaneously and consider the higher physiological activity of zeaxanthin, and the closer to macular center it is, the higher amounts of zeaxanthin is. So the supplementary amount of zeaxanthin should be greater than that of lutein, especially a total daily intake of lutein and zeaxanthin is larger. It can ensure to ingest larger zeaxanthin with high biological activity at the time of ingesting enough lutein.

In addition, the formation mechanism of AMD disease is mainly retinal pigment epithelial cells damaged by high-energy blue light or free radicals oxidative damage, to cause pulpiness or hemorrhagic detachment and lead to formation of choroidal neovascularization or drusen. So it is helpful to appropriately supple some dietary ingredient preventing neovascularization formation when supplying lutein and zeaxanthin. The tea extract just has the effect. Clinical studies have especially shown that EGCG in tea extracts can play a role in inhibiting neovascularization formation by inhibiting neovascularization formation related factor and its receptor inhibiting proliferation, migration, tube formation of vascular cells and induction apoptosis, etc. The AMD disease can be prevented or treated through synergistic effects of tea extract and lutein and zeaxanthin.

Comparing with the control group, the change of MPOD of the test groups has significant differences. The effect of supplying lutein group (test group II) is better than that of supplying zeaxanthin group (test group I) when supplying lutein or zeaxanthin alone. It may be because partial lutein can be translated into zeaxanthin in body, to reach synergistic effects. But, no synergistic effects reaches if supplying zeaxanthin alone, without lutein in body. The rising effect of MPOD when supplying lutein and zeaxanthin is superior to that of supplying lutein or zeaxanthin alone. And the increased effect of MPOD when supplying the weight ratio of zeaxanthin to lutein being 3:1 (test group IV) is superior to that of the test group having the weight ratio of lutein to zeaxanthin being 3:1 (test group III), The two test groups have significant differences. The increased effect of MPOD for intaking a certain amount of EGCG is the best during supplying the mixture comprising the weight ratio of zeaxanthin to lutein being 3:1 (test group V). All of these means that the synergistic effect of the three components is obvious.

Therefore, the present invention is to supply the amount of lutein and zeaxanthin in body especially in the macular through ingesting combination of lutein and zeaxanthin. Especially in view of the importance role of zeaxanthin in protecting the visual health, the weight ratio of zeaxanthin to lutein in this composition is generally more than 1, usually up to 3:1, And in view of the formation mechanism of age-related macular degeneration (AMD), a certain antioxidant dietary supplement such as tea extracts, especially EGCG, is added into the composition of lutein and zeaxanthin, to prevent or inhibit formation of neovascularization. The composition of the present invention can inhibit formation of neovascularization in the retina, in order to achieve effects of preventing or treating age-related macular degeneration (AMD).

DETAILED DESCRIPTION OF THE INVENTION AND PREFERRED EMBODIMENTS THEREOF

Figure 1:
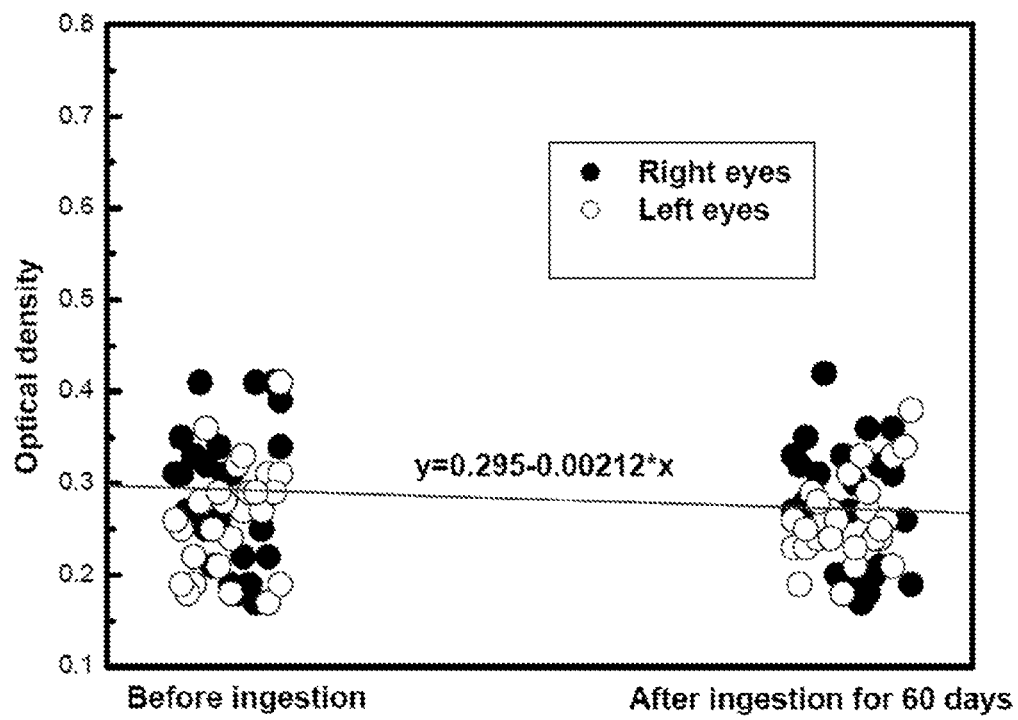
FIG. 1 shows the changing rate of MPOD average value within five days before and after feeding placebo for the control group.

The features of the present invention will be more clearly understood by reference to the following embodiments, which are not to be construed as limiting the present invention.

EXAMPLE 1

Human Beings Test of Lutein, Zeaxanthin, EGCG for Treating or Preventing Age-Related Macular Degeneration (AMD)

208 patients (males 88, females 120), being more than 55 years old and diagnosed with AMD were selected for this test, according to voluntary principles, with the exception of the following subjects: those who have certain ophthalmic disease that may affect the testing results; those who have administered relevant drugs, health products or applied other treatments for long or short time affecting determination for results; those who do not confirm to inclusion criteria, and do not feed tested drug according to requirement, or have incomplete information affecting efficacy or safe-determination.

Control groups and intervention groups were established in tests, wherein 31 subjects were randomly selected to administer placebo in a control group. Intervention groups were further divided into five groups (I, II, III, IV, V). Subjects in each of intervention groups were successively administered by drug chewing tablets as shown in Table 1 for 60 days, once per day, one tablet once. The test is adopted for comparing before-treatment and after-treatment as well as comparing among groups. 16 subjects didn't complete the test during the test due to various of reasons. The churn rate of subjects is 7.7%. When the test is completed the amount of subjects in each group is shown in Table 1.

TABLE 1

Group of Human Test and Formulation of Feeding Tablet

| Group | Number | Formulation of feeding tablet |
| --- | --- | --- |
| control group | 28(male 10, female 18) | placebo |
| test group I | 32(male 13, female 19) | 32 mg lutein |
| test group II | 33(male 15, female 18) | 32 mg zeaxanthin |
| test group III | 32(male 14, female 18) | 24 mg lutein and 8 mg zeaxanthin |
| test group IV | 32(male 13, female 19) | 8 mg lutein and 24 mg zeaxanthin |
| test group V | 35(male 13, female 22) | 8 mg lutein, 24 mg zeaxanthin and 120 mg EGCG |

Wherein:

1, The active ingredient of the formulation includes lutein with CarolGold™ 10% TAB and zeaxanthin with Carol-Zea™ 10% TAB, and the content of EGCG purchased from RongKai Plant Extracts Co., LTD is 95%. Except active ingredients such as lutein, zeaxanthin and EGCG, the rest is xylitol and necessary auxiliary materials of tablets such as hydroxylmethyl cellulose, microcrystalline cellulose, magnesium stearate etc. Firstly, EGCG, hydroxymethyl cellulose and microcrystalline cellulose are mixed and wet granulated to obtain granuls, the granuls are mixed with lutein, zeaxanthin 10% TAB and magnesium stearate, and then are tabletted after sifting through 30 mesh sieve to obtain chewable tablets, the total weight of each tablet is 850 mg.

2, Appearance, color and tablet weight of placebo are the same as these of feeding tablets.

Subjects are respectively fed with chewable tablets and placebo tablets, and the macular pigment optical density (MPOD) in the left and right eyes is measured by a heterochromatic flicker photometry every day in five days before feeding and the last five days before finishing feeding. The treatment effect of the chewable tablets for treating macular degeneration is evaluated by comparing the increased rate of the average value of MPOD for each patient in the last five days after feeding chewable tablets comprising lutein and zeaxanthin for two months, with the average value of MPOD for each patient in five days before feeding chewable tablets.

Each index including security index and functional index is measured once at the beginning and at the end of the feeding test. Security index includes regular physical examination, blood, urine, stool routine examination, blood biochemical criterion examination, type-B ultrasound, chest X-ray, electrocardiographic examination and other corresponding examinations. Functional index includes ocular symptom examination as follows: inquiring case history; observing subjective symptom of eyes such as eye swelling, ophthalmalgia, photophobia, visual blurring, eye dryness etc.; data processing such as calculating and analyzing data by using a statistical software STATE6.0, Paired t test is used for self-control data, and group t test is used for comparison between mean values of two groups. The latter needs homogeneity test for variance to do suitable variable transformation for the data with non-normal distribution or variance nonhomogeneity until the normal variance homogeneity is met, and then the transformed data is used for t test. If the transformed data could not meet normal variance homogeneity, t test or rank-sum test is used; but the coefficient of variation is too large, for example, CV>50%, the rank sum test should be used. $X^2$ test is used for functional indexes.

Figure 2:
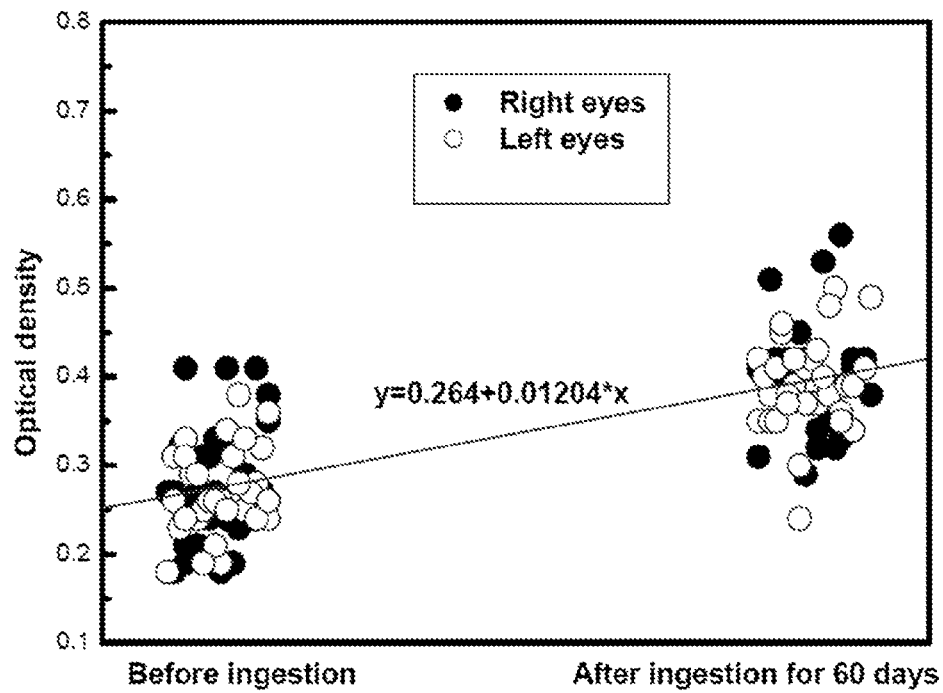
FIG. 2 shows the changing rate of MPOD average value within five days before and after feeding lutein for the intervention group.
Figure 3:
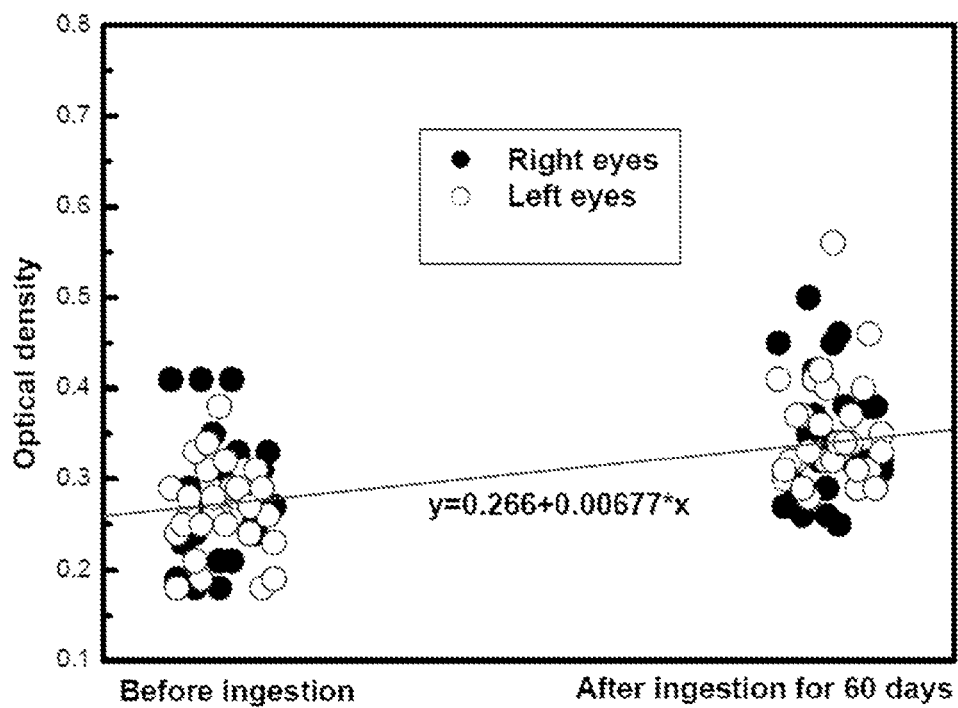
FIG. 3 shows the changing rate of MPOD average value within five days before and after feeding zeaxanthin for the intervention group.
Figure 4:
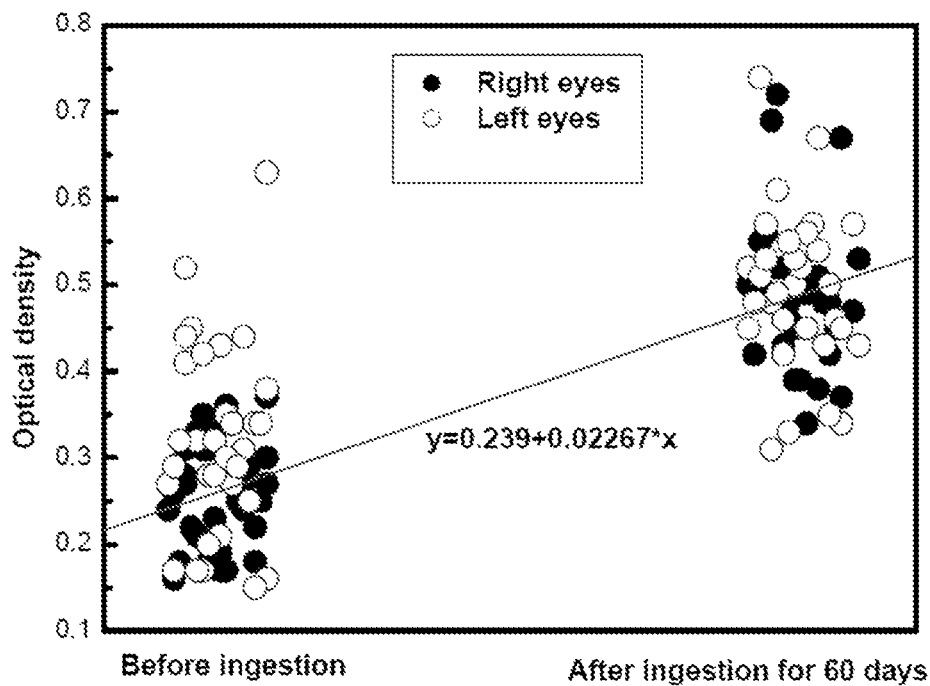
FIG. 4 shows the changing rate of MPOD average value within five days before and after feeding the composition of lutein and zeaxanthin with the proportion of 3:1 for the intervention group.
Figure 5:
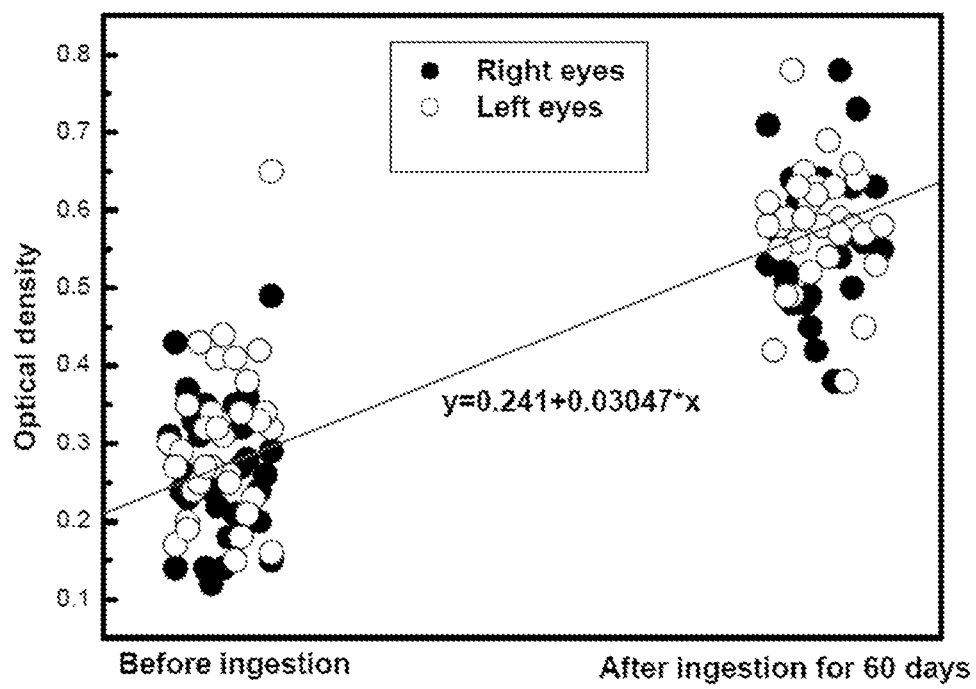
FIG. 5 shows the changing rate of MPOD average value within five days before and after feeding the composition of lutein and zeaxanthin with the proportion of 1:3 for the intervention group.
Figure 6:
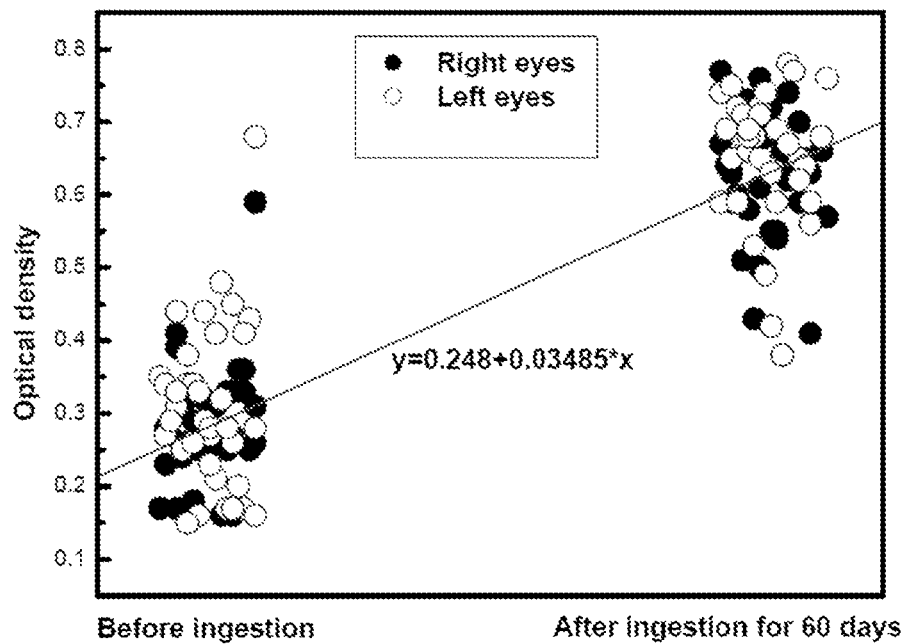
FIG. 6 shows the changing rate of MPOD average value within five days before and after feeding the composition comprising lutein and zeaxanthin with the proportion of 1:3, as well as the antioxidants EGCG for the intervention group.

Measures of various of biochemical indicators show after feeding chewable tablets comprising lutein and zeaxanthin that no adverse reactions occurs. The changes on the average of macular pigment optical density in the left and right eyes for the control group and test group in the five days before and after the test are shown in FIG. 1 to FIG. 6. It can be seen from the Figures that comparing with the control group, the macular pigment optical density (MPOD) of the test group increases significantly, but the variation of MPOD in each test group for feeding different formulas or proportions of lutein to zeaxanthin is not identical. For instance, for the variation of MPOD in the right eye, the MPOD value of the right eye obtained by each test group before the test and after feeding is proceeded with linear regression and got an equation y=a+b*x, intercept a-value of each group reflects an average MPOD in the right eye of each group member before feeding tablets. And it can be seen that little difference between each groups is present; b-value reflects variation tendency of MPOD in the right eye after feeding tablets for 90 days and before feeding tablets, the higher the b-value is, the more obvious the MPOD variation is. The values of a and b representing MPOD variation in the right eye of each group after liner regression are shown in Table 2.

TABLE 2

Values of a and b Representing MPOD Variation in the Right Eye of Each Group after Linear Regression

| group | a | b ($\times 10^{-2}$) |
| --- | --- | --- |
| control group | 0.295 | 0.212 |
| test group I | 0.266 | 0.677 |
| test group II | 0.264 | 1.204 |
| test group III | 0.240 | 2.267 |
| test groupIV | 0.241 | 3.047 |
| test group V | 0.248 | 3.485 |

It can be seen from Table 2 that comparing with the control group, the variation of MPOD of each test group has significant differences, the effect of supplying zeaxanthin group (test group II) is better than that of supplying lutein group (test group I), when supplying lutein or zeaxanthin alone. It is probably because partial lutein can be translated into zeaxanthin in the body, so as to play synergistic effects. Merely zeaxanthin without lutein is in the body when supplying zeaxanthin alone, and consequently it does not reach synergistic effects. The rising effect of MPOD when supplying the composition comprising lutein and zeaxanthin is better than that of supplying lutein or zeaxanthin alone. The increased effect of MPOD when supplying the weight ratio of zeaxanthin to lutein being 3:1 (test group IV) is better than that of the test group supplying the weight ratio of lutein to zeaxanthin being 3:1 (test group III). The two test groups have significant differences. The increased effect of MPOD for intaking a certain amount of EGCG is optimal, when supplying the mixture comprising zeaxanthin to lutein being 3:1 (test group V). This means that the synergistic effect of the three components comprising zeaxanthin, lutein and EGCG is very obvious.

EXAMPLE 2

A Soft Capsule Consisting of the Following Components

| Component | Amount (mg/grain) |
|---|---|
| lutein | 2.0 |
| (3R,3'S, meso)- zeaxanthin | 4.0 |
| EGCG (more than 95%) * | 20.0 |
| Beta- carotene | 6.0 |
| d-alpha tocopheryl acetate | 100.0 |
| polyunsaturated fatty acids DHA | 20.0 |
| safflower oil | 118.0 |
| summation | 250.0 |

* EGCG is purchased from RongKai Plant Extracts Co., LTD.
Usage: twice per day, a grain once.

EXAMPLE 3

A Hard Capsule Consisting of the Following Components

| Component | Amount (mg/grain) |
|---|---|
| lutein | 6.0 |
| (3R,3'R)- zeaxanthin | 6.0 |
| EGCG (more than 80%)* | 10.0 |
| retinol acetate power 500,000 IU | 12.0 |
| dl-alpha tocopheryl acetate powder 50% | 20.0 |
| ascorbic acid power | 100.0 |
| polyunsaturated fatty acids EPA power | 15.0 |
| copper | 15.0 |
| zinc | 40.0 |
| L-selenomethionine | 0.15 |
| lecithin | 75.85 |
| summation | 300.0 |

*EGCG is purchased from RongKai Plant Extracts Co., LTD
Usage: once per day, a grain once.

EXAMPLE 4

A Tablet Consisting of the Following Components:

| Component | Amount (mg/tablet) |
|---|---|
| lutein ester | 120.0 |
| zeaxanthin ester | 60.0 |
| tea polyphenol * | 100.0 |
| beta-carotene | 6.0 |
| blueberry extract (antioxidant) | 150 |
| magnesium stearate | 5.6 |
| modified starch | 158.4 |
| summation | 600.0 |

* The content of tea polyphenols is more than 80%, and purchased from Jin Cheng Biotechnology.
Usage: once per day, a tablet once.

EXAMPLE 5

A Hard Capsule Consisting of the Following Components

| Component | Amount (mg/grain) |
|---|---|
| lutein | 20.0 |
| zeaxanthine | 20.0 |
| tea extract* | 200.0 |
| dl-alpha tocopheryl acetate powder 50% | 40.0 |
| blueberry polyphenol * | 79.85 |
| zinc | 40.0 |
| L- selenomethionine | 0.15 |
| summation | 400.0 |

The content of tea polyphenols in tea extract is more than 80%, and purchased from Jin Cheng Biotechnology. The content of blueberry polyphenols is more than 25%, and purchased from Ling Ge Bei Organic Food Co., LTD.

Usage: once per day, a grain once.

Although the invention contents and embodiments of the present invention are to prove practical application of technical solution of the present invention, it should be understood that the present invention is not limited to such preferred embodiments and procedures set forth above. It will be apparent for person skilled in the art that various substitution, modifications and changes may be thereto without departing from the scope and spirit of the present invention.

The invention claimed is:

1. A composition for treatment or prevention of age-related macular degeneration, comprising effective amounts of lutein, zeaxanthin and epigallocatechin gallate, wherein the weight ratio of zeaxanthin to lutein is in a range of 2:1-3:1.

2. The composition according to claim 1, wherein the amount of zeaxanthin or lutein is respectively 2 mg~120 mg.

3. The composition according to claim 2, wherein the amount of zeaxanthin or lutein is respectively 6 mg~20 mg.

4. The composition according to claim 3, wherein zeaxanthin is (3R, 3'R)-zeaxanthin or (3R, 3'S)-zeaxanthin extracted from plants or obtained by chemical synthesis.

5. The composition according to claim 3, wherein lutein and zeaxanthin is respectively in the form of free crystal or fatty acid ester.

6. The composition according to claim 1, wherein the amount of epigallocatechin gallate is 10 mg~200 mg.

7. The composition according to claim 6, wherein the amount of epigallocatechin gallate is 20 mg~120 mg.

8. The composition according to claim 1, further comprising vitamins, antioxidants and/or trace element, wherein the vitamins is selected from a group comprising vitamin C, vitamin E , natural vitamin E and vitamin A, wherein the antioxidants is selected from a group comprising beta-carotene, polyunsaturated fatty acids and/or plant extract blueberry polyphenols, and wherein the trace element is selected from a group comprising copper, zinc and/or selenium.

* * * * *